US00PP19545P2

(12) United States Plant Patent
Bradford

(10) Patent No.: US PP19,545 P2
(45) Date of Patent: Dec. 2, 2008

(54) PEACH TREE NAMED 'PRINCESS TIME'

(50) Latin Name: *Prunus persica*
Varietal Denomination: Princess Time

(76) Inventor: Lowell Glen Bradford, 10237 E, Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,897

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP7,953 P 8/1992 Bradford

*Primary Examiner*—Annette H Para
*Assistant Examiner*—S. B. McCormick-Ewoldt

(57) ABSTRACT

The present invention relates to a new and distinct variety of peach tree, *Prunus persica,* broadly characterized by a medium size, vigorous, hardy, self-fertile, productive and regular bearing tree. The variety blooms during the early season and requires about 500 chilling hours. The fruit matures under the ecological conditions described in early June, with first picking on Jun. 1, 2007. The fruit is uniformly large in size, acidic and sweet in flavor, globose in shape, clingstone in type, firm and melting in texture, yellow in flesh color, and mostly red in skin color.

1 Drawing Sheet

Botanical classification: *Prunus persica.*
Variety denomination: 'PRINCESS TIME'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Princess Time'.

The present variety was hybridized by me in 2001 as a first generation cross using '1P1152' (unpatented) nectarine as the selected seed parent and an unnamed low chill peach as the selected pollen parent. I used embryo rescue techniques to germinate the seeds from the fruit of this cross, grew them as seedlings on their own root in my greenhouse, and upon reaching dormancy transplanted them to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Crimson Lady' (U.S. Plant Pat. No. 7,953) peach by producing peaches that are firm, yellow in flesh color, mostly red in skin color, and ripen in early June, but is distinguished therefrom by requiring less chilling hours, by blooming in the early season, and by producing fruit that is larger in size, melting instead of non-melting in texture, and that has a more traditional peach flavor.

SUMMARY OF VARIETY

In summary, the present variety is characterized by a medium size, vigorous, hardy, self-fertile, productive and regular bearing tree. The variety blooms during the early season and requires about 500 chilling hours. The fruit matures under the ecological conditions described in early June, with first picking on Jun. 1, 2007. The fruit is uniformly large in size, acidic and sweet in flavor, globose in shape, clingstone in type, firm and melting in texture, yellow in flesh color, and mostly red in skin color.

DRAWING

The accompanying photograph consists of four whole fruits positioned to display the characteristics of the skin color and form, one sliced fruit to reveal the flesh, a freshly cleaned stone, two insets to reveal buds and a blossom, and a typical tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe one Jun. 6, 2007, on the original tree during its sixth growing season. The blossom and flower descriptions were made the previous blooming season. All major color code designations are by reference to the Inter-Society Color Council, National Bureau of Standards. Common color names are also used occasionally.

Parentage

Seed Parent: 1P1152 nectarine (unpatented).
Pollen Parent: Unnamed peach.

Tree

Size: Medium, reaching and maintaining a height of 12' [3.66 m.] and a spread of 9' [2.74 m.] after six growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase form.
Hardiness: Hardy with respect to central California winters.
Chilling Requirement: About 500 hours.
Heat Tolerance: Observed to perform adequately in typical central California climatic conditions, which typically include extended periods of heat.
Drought Tolerance: Variety is developed for commercial orchards and requires regular irrigation.
Production: Very productive, thinning usually necessary.
Fertility: Self-fertile.
Bearing: Regular bearer, with no crop failures observed.
Trunk:
*Size.*—Medium, reaching a maximum diameter of 4½" [114 mm.] after the sixth growing season.
*Texture.*—Shaggy.
*Bark color.*—A Deep brown [56. deep Br] and Grayish brown [61. gy.Br] variegation.
*Lenticels.*—Approximate Number Per Square Inch: 8. Color: Deep orange yellow [69. deep OY]. Average Size: ⅜" [9.5 mm.]. Shape: Eye-shaped, elongated.
Branches:
*Size.*—Diameter of limb is 2½" [63.5 mm.] measured 12" above the crotch, 1¾" [44.5 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. Older Wood: Moderate yellowish brown [77. m.yBr].
*Lenticels.*—Number Per Square Inch: More than 60 on second year wood. Color: Dark orange yellow [72. d.OY]. Average Size: 1/64" [0.4 mm.). Shape: Elongated, rectangular.
Leaves:
*Size.*—Large. Average Length: 6¾" [172 mm.]. Average Width: 1⅝" [41 mm.].
*Arrangement.*—Alternate.
*Thickness.*—Medium.
*Form.*—Elliptical.
*Apex.*—Acuminate.
*Base.*—Acute with an average angle of 75 degrees.
*Surface.*—Smooth.
Color. —Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Strong yellow green [117. s.YG].
*Stipules.*—Number: 2 per leaf, up to 6 per growing tip. Average Length: 5/16" [7.9 mm.]. Color: Very yellow green [115. v.YG] becoming Strong brown [55. s.Br] with age.
*Glands.*—Number: Mostly 2 per leaf. Position: Alternately positioned at the intersection of the petiole and the leaf blade. Size: Small. Form: Globose. Color: Strong yellow green [117. s.YG] becoming Moderate reddish brown [43. m.rBr] in the center with age.
*Leaf buds.*—Pointed, medium.
Flower Buds:
*Hardiness.*—Hardy, with respect to central California winters.
*Diameter.*—Typically ⅜" [9.5 mm.] 1 week before bloom.
*Length.*—Typically 9/16" [14.3 mm.] 1 week before bloom.
*Form.*—Not appressed.
*Surface.*—Pubescent.
*Tip color.*—Moderate purplish pink [250. m.ppk].
Flowers: Perfect, complete, perigynous, usually a single pistil, typically thirty or more stamens, five sepal and petal locations alternately positioned.
*Type.*—Showy, large.
*Average flower diameter.*—2 1/16" [52.4 mm.].
*Number of petals.*—Usually five, extra petal fragments commonly occur, double blossoms rarely observed.
*Petal shape.*—Circular to oval.
*Petal margin.*—Entire, somewhat wavy, occasional notches.
*Average petal diameter.*—13/16" [20.6 mm.].
*Average petal length.*—⅞" >[22.2 mm.].
*Petal apex.*—Rounded.
*Petal base.*—Rounded to somewhat truncate.
*Petal color.*—Pale pink [7. p.Pk] toward the apex, Light purplish pink [249. l.pPk] toward the base.
*Anther color.*—Strong reddish orange [35. s.rO] over a Light yellow [86. l.Y] center at bloom onset.
*Stigma color.*—Pale yellow green [121. p.YG].
*Sepal color.*—Dark purplish red [259. d.pR].
*Sepal length.*—15/64" [6 mm.].
*Sepal width.*—3/16" [5 mm.].
*Average pistil length.*—13/16" [20.6 mm.].
*Average stamen length.*—9/16" [14.3 mm.].
*Fragrance.*—Moderate.
*Blooming period.*—Early to medium, with days before 'Rose Diamond' (U.S. Plant Pat. No. 7,421) nectarine.
*Onset of bloom.*—One percent on Feb. 25, 2007.
*Date of full bloom.*—Mar. 4, 2007.
*Duration of bloom.*—One to two weeks, dependent on ambient temperature.
*Number per cluster.*—1 to 3 with single flowers most common.

FRUIT

Maturity when described: Firm ripe, Jun. 6, 2007.
Date of first picking: Jun. 1, 2007.
Date of last picking: Jun. 10, 2007.
Size: Uniform, large.
*Average diameter axially.*—2 15/16" [74.8 mm.].
*Average diameter across suture plane.*—3"[76 mm.].
*Average diameter across cheek plane.*—3¼" [82.4 mm.].
*Typical weight.*—7.6 ounces (215 grams).

Form: Uniform, globose, symmetrical.
*Longitudinal section form.*—Oval to round.
*Axial view.*—Round to elliptical.
Suture: Extends from the base to just past the pistil point, some Pale yellow [89. p.Y] stitching present.
*Near the base.*—A shallow, sharp groove.
*Along the side.*—A shallow trough.
*Near the apex.*—A shallow groove.
Ventral surface: Rounded, lipped stronger toward the apex.
Lips: Mostly equal.
Cavity: Flaring, elongated in the suture plane, suture showing on both sides, Light greenish yellow [101. l.gY] stem markings typical.
*Depth.*—½" 12.7 mm.].
*Breadth.*—1⅛" [28.6 mm.].
Base: Truncate, slightly cordate if viewed parallel to suture.
Apex: Rounded with an indented area around the pistil point.
Pistil Point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to the flesh.
*Astringency.*—Moderate.
Tendency to crack. —None observed in dry season.
*Color.*—Very red [11. v.R] to Very deep red [14. v.deep R] over a Deep yellowish pink [27. deep yPk] background.
*Down.*—Moderate, will roll up when rubbed.
Flesh:
*Color.*—Light yellow [86. l.Y] with Strong red [12. s.R] bleeding close to the stone.
*Surface of pit cavity.*—Pale yellow [89. p.Y] broken fibers when twisted from stone.
*Amygdalin.*—Moderate.
*Juice.*—Moderate, rich.
*Texture.*—Firm, melting.
*Fibers.*—Abundant, fine, tender.
*Ripens.*—Earlier toward the apex.
*Flavor.*—Traditional peach flavor, acidic and sweet, typically 14 brix.
*Aroma.*—Moderate.
*Eating quality.*—Excellent.

STONE

Type: Clingstone.
Form: Oval.
Hilum: Narrow.
Base: Rounded.
Apex: Acuminate with an average angle of 70 degrees.
Sides: Equal.
Surface: Irregularly furrowed and ridged toward the apex and ventral edge, randomly pitted toward the base.
Ridges: Rounded.
External Color: Moderate orange yellow [71. m.OY].
Pit Wall Color When Cracked: Pale orange yellow [73. p.OY].
Cavity Surface Color: Light yellowish brown [76. l.yBr].
Average Pit Wall Thickness: ¼" [6.4 mm.].
Average Width: 15/16" [23.8 mm.].
Average Length: 1¼" [31.8 mm.].
Average Breadth: ⅝" [15.9 mm.].
Tendency To Split: Slight.
Kernel:
*Form.*—Oval.
Skin color. —Pale yellow [89. p.Y] when first removed.
*Pellicle color.*—Grayish yellow [90. gy.Y].
*Vein color.*—Yellowish gray [93. yGray].
*Taste.*—Bitter.
*Viable.*—Only by utilizing embryo rescue techniques.
*Average width.*—7/16" [11.1 mm.].
*Average length.*—11/16" [17.5 mm.].
*Amygdalin.*—Moderate.

Use

Market: Fresh market and long distance shipping.
Keeping Quality: Good, fruit quality observed to remain in good condition after 17 days in standard cold room at 36° Fahrenheit [2° Celsius].
Shipping Quality: Good.
Resistance To Insects: No unusual susceptibilities noted.
Resistance To Diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to 'Crimson Lady' (U.S. Plant Pat. No. 7,953) peach by producing peaches that are firm, yellow in flesh color, mostly red in skin color, and ripen in early June, but is distinguished therefrom by requiring less chilling hours, by blooming in the early season, and by producing fruit that is larger in size, melting instead of non-melting in texture, and that has a more traditional peach flavor.

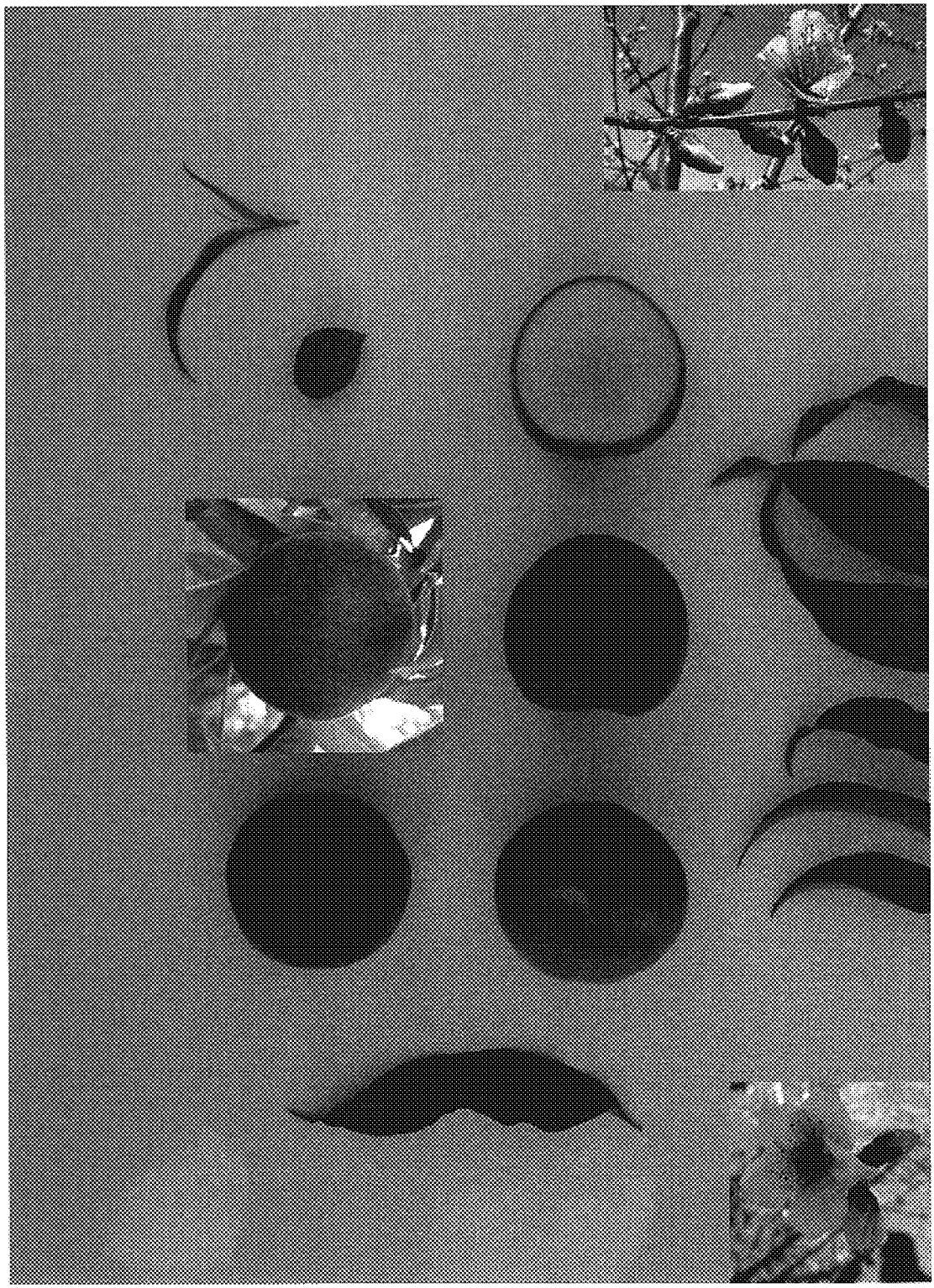

* * * * *